United States Patent [19]

Mark et al.

[11] Patent Number: 5,229,136
[45] Date of Patent: Jul. 20, 1993

[54] LOW CALORIC DENSITY ENTERAL FORMULATION DESIGNED TO REDUCE DIARRHEA IN TUBE-FED PATIENTS

[75] Inventors: David A. Mark, Oak Park; Lance Stalker, Grayslake, both of Ill.

[73] Assignee: Clintec Nutrition Co., Deerfield, Ill.

[21] Appl. No.: 887,361

[22] Filed: May 21, 1992

[51] Int. Cl.$^5$ .............................. A61K 35/20
[52] U.S. Cl. ................ 424/535; 424/195.1; 426/72; 426/583; 426/804
[58] Field of Search ............ 424/195.1, 535; 426/72–74, 583, 601–602, 648, 656–658, 800–804

[56] References Cited

U.S. PATENT DOCUMENTS 4,670,268  6/1987  Mahmoud .................. 426/72
4,959,350  9/1990  Frokjaer et al. ............. 514/2
4,999,197  3/1991  Wursch ..................... 424/195.1

Primary Examiner—Marianne M. Cintins
Assistant Examiner—Michael B. Hydorn
Attorney, Agent, or Firm—Hill, Steadman & Simpson

[57] ABSTRACT

The present invention provides an enteral product for providing nutritional requirements to a patient comprising: a caloric content of less than 1.00 Kcal/ml;. an osmolality of less than 300 mOsm; and a fiber content of preferably greater than 15 gms/liter. Additionally, the present invention provides a method of providing nutrition to a patient through a tube-fed enteral product and reducing the risk of diarrhea comprising the steps of: providing a sterile enteral product, that does not require diluting, having an osmolality of less than 300 mOsm and a caloric content of less than 1.0 Kcal/ml, but, having a fiber content of greater than 15 gms/liter; and enterally administering the product to a patient.

14 Claims, No Drawings

LOW CALORIC DENSITY ENTERAL FORMULATION DESIGNED TO REDUCE DIARRHEA IN TUBE-FED PATIENTS

BACKGROUND OF THE INVENTION

The present invention relates generally to the feeding of a patient, through a tube, with an enteral product. More specifically, the present invention relates to the prevention of diarrhea in a tube-fed patient.

It is known to feed patients, requiring nutrition in a hospital or other healthcare setting (including a home), with an enteral or parenteral nutritional solution. Parenteral nutritional solutions include solutions that are infused into the venous system of a patient through an IV system. Enteral products include products that are fed to a patient through a tube that is fed through the nasogastric system.

Although enteral products fed through a nasogastric tube can provide a patient with total nutritional requirements, there are, in certain patients, some side effects from such feedings. In this regard, it is known that certain patients will experience diarrhea when tube fed enteral nutritional products.

Diarrhea is cited as the most common cause of interrupted tube feeding. Likewise, diarrhea is cited as the most frequent complaint of tube-fed patients. Many hospital nurses, dietitians, and physicians have identified the reduction of diarrhea as being one of the most desirable areas of patient care. In this regard, diarrhea effects approximately 10 to 40% of the tube-fed hospitalized patients. It is also know, to a lesser extent that tube-fed patients experience nausea and abdominal distension.

To help to reduce the incidence of diarrhea, it is known to put fiber or other anti-diarrhea composition in enteral formulations. Due to problems with keeping a particulate substance in suspension, only a certain amount of fiber can be loaded in a typical enteral formulation. For example, typical fiber containing enteral products include 14 grams of insoluble soy polysaccharide (fiber) per liter and have a caloric density of 1.0 Kcal/ml.

The addition of insoluble fiber, however, does not eliminate the incidence of diarrhea. Therefore, it is common practice in U.S. hospitals, when faced with a tube-fed patient with diarrhea, to initially reduce the flow rate and/or concentration of the enteral product. It is expected that because fluid volume and osmolality are reduced, the diarrhea will also be reduced.

Accordingly, hospitals dilute such enteral products to three-quarter to one-half strength. This reduces nutrient load, theoretically reducing malabsorption, and also reduces osmolality. Although improvements should be expected when the fluid volume and osmolality of an enteral product are reduced, to achieve the reduced osmolality, the hospital merely dilutes the product. For example, the product is mixed with water so as to be diluted to 50%.

The disadvantage of this procedure is that the fiber, or other anti-diarrhea composition, in the enteral product is likewise reduced. Therefore, the dilution of the product does not always result in a reduction in the severity of the diarrhea. Furthermore, the dilution process can compromise the sterility of the enteral product. Still further, because the product is diluted, essential vitamins and minerals are not supplied in adequate quantity.

SUMMARY OF THE INVENTION

The present invention provides an enteral nutritional product that can be used to tube feed a patient and reduce the incidence or severity of diarrhea. To this end, the present invention provides an enteral product that meets most of the daily nutritional requirements of hospitalized patients. However, the product has a sufficiently reduced caloric density and osmolality, but a sufficiently high fiber content, to reduce or eliminate the risk of diarrhea.

To this end, the present invention provides an enteral product for providing nutritional requirements to a patient comprising: a caloric content of less than 1.00 Kcal/ml; an osmolality of less than 300 mOsm; and a fiber content of at least 14 gms/liter and preferably greater than 15 gms/liter.

In an embodiment, the product includes approximately 18 to about 25% of the total calories as protein.

In an embodiment, the product includes approximately 35 to about 50% of the total calories as fat.

In an embodiment, the fiber includes one or more components chosen from the group consisting of: insoluble soy polysaccharide; insoluble pectin; hydrolyzed plant gums; carob pod; and tannin-enriched extract of carob pod.

Additionally, the present invention provides a method of providing nutrition to a patient through a tube-fed enteral product and reducing the risk of diarrhea comprising the steps of: providing a sterile enteral product, that does not require diluting, having an osmolality of less than 300 mOsm and a caloric content of less than 1.0 Kcal/ml but having a fiber content of greater than 15 gms/liter; and enterally administering the product to a patient.

An advantage of the present invention is that it provides a prediluted product with a high fiber content.

Furthermore, an advantage of the present invention is that it provides a sterile closed system that does not have to be diluted before use.

Still further, an advantage of the present invention is that it provides a product having a higher than typical protein content, as a percentage of calories, to help meet protein requirements in a calorie reduced product.

Moreover, an advantage of the present invention is that the composition has a vitamin and mineral composition which meets vitamin and mineral requirements in a calorie reduced product.

Additionally, an advantage of the present invention is that the composition has a higher lipid content that helps to reduce osmolality and slow transit time.

Additional features and advantages of the present invention are described in, and will be apparent from, the detailed description of the presently preferred embodiments.

DETAILED DESCRIPTION OF THE PRESENTLY PREFERRED EMBODIMENTS

The present invention provides an enteral product suitable for tube feeding that provides most of the daily nutritional requirements of hospitalized and nursing home patients. The product has a caloric density of less than 1.0 Kcal/liter. In a preferred embodiment, the present invention provides a product with a caloric density of approximately 0.5 to about 0.8 Kcal/ml.

The osmolality of the product of the present invention is less than 300 mOsm. Preferably, the osmolality is approximately 100 to about 250 mOsm.

In order to provide sufficient nutritional requirements, the present invention includes a protein content that comprises greater than 17% of the total calories of the product. Preferably, the protein content is approximately 18 to about 25% of the total calories of the product. The protein content can be provided by, for example, casein, hydrolyzed casein, hydrolyzed whey protein, or hydrolyzed soy protein.

Additionally, the present invention has a fat content that comprises greater than 33% of the total calories of the product. Preferably, the fat content of the product is approximately 35 to about 50% of the total calories. The fat content can be provided by, for example, a blend of medium chain triglycerides and soy oil.

In order to provide an anti-diarrhea product, the present invention includes a fiber content of at least 14 gms/liter. Preferably, the product has a fiber content of greater than 15 gms/liter. As used in the patent application, "fiber" includes, inter alia, the following: insoluble soy polysaccharide; soluble pectin; hydrolyzed plant gums; carob pod, e.g., carob pod powder; or a tannin-enriched extract of carob pod.

If desirable, the formulation can include arginine, ornithine, cysteine, L-2-oxothiazolidine-4-carboxylate, and/or omega-3 rich lipids, such as marine oil or canola oil.

Due to the structure of the present invention, the typical hospital practice of diluting an enteral product to ½ to ¾ strength is not necessary. The composition already includes a reduced nutrient load.

However, in contrast to dilutions that are made in the hospital, the fiber content of the product is not reduced. Indeed, the product of the present invention provides a fiber content that is greater than normal. Because the caloric density is reduced, the inventor of the present invention has found that the amount of fiber can be increased. Furthermore, the sterility of the closed system of the product as manufactured is maintained because dilution is not required.

The present invention also provides, in a preferred embodiment, a protein content that is greater than protein requirements in a typically calorie reduced product. Likewise, the present invention includes a higher lipid content. This reduces osmolality and slows transit time period.

The addition of arginine, ornithine, cysteine, L-2-oxothiazolidine-4-carboxylate, and/or omega-3 rich lipids can also provide an advantage in normalizing gut mucosal structure and function. If desirable, a carob pod product, e.g., carob pod powder, can be added. The carob pod product provides anti-diarrhea characteristics. Additionally, the carob pod product provides anti-bacterial and anti-viral activity. The carob pod product can be constructed in accordance with U.S. Pat. No. 4,999,197, the disclosure of which is incorporated herein by reference.

Furthermore, the present invention can include the necessary USRDA of vitamins and minerals. This provides an advantage over a diluted product wherein the necessary USRDAs of vitamins and minerals is not provided. However, preferably, a reduced level of magnesium is provided. Rather than the USRDA of 400 mg/day of magnesium, preferably only 150–250 mg/day will be provided.

By way of example, and not limitation, examples of products of the present invention are as follows:

EXAMPLE NO. 1

| Caloric density 0.75 kcal/ml | | |
|---|---|---|
| Protein | = | casein |
| | | at 25% kcal of the product |
| Lipid | = | 50% MCT; 50% canola |
| | | at 40% kcal of the product |
| Carbo | = | Malto dextrin |
| | | at 35% kcal of the product |
| Fiber | = | 20 gms/liter |
| | | (10 gms soy polysaccharide; |
| | | 10 gms tannin-rich carob extract) |
| Vit/Min | = | delivers USRDA in 1500 ml with the exception that magnesium is at 250 mg/1500 ml |

EXAMPLE NO. 2

| Caloric density 0.5 kcal/ml | | |
|---|---|---|
| Protein | = | hydrolyzed whey, at 20% kcal of the product |
| Lipid | = | 70% MCT; 30% Canola |
| | | at 40% kcal of the product |
| Carbo | = | maltodextrin |
| | | at 40% kcal of the product |
| Fiber | = | 20 gms/liter |
| | | (10 gms tannin-rich carob extract; |
| | | 5 gms soluble pectin; |
| | | 5 gms soy polysaccharide) |
| Vit/Min | = | delivers USRDA in 1500 ml with the exception that magnesium is at 250 mg/1500 ml |

In use, for the average patient, approximately 1500 ml of products of either Example 1 or 2 would be given per day. Of course, depending on patient requirements and other adjunct therapy and solutions that are used more or less product can be given.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

We claim:

1. An enteral product for providing nutritional requirements to a patient comprising:
   a protein, fat, and carbohydrate source;
   the enteral product having a caloric content of less than 1.00 Kcal/ml and an osmolality of less than 300 mOsm; and
   a fiber content of at least 14 gms/ml.

2. The enteral product of claim 1 including approximately 18 to about 25% of the total calories as protein.

3. The enteral product of claim 1 including approximately 35 to about 50% of the total calories as fat.

4. The enteral product of claim 1 wherein fiber includes one or more components selected from the group consisting of: insoluble soy polysaccharide; pectin; hydrolyzed plant gum; carob pod; and tannin-enriched extract of carob pod.

5. The enteral product of claim 1 wherein the composition includes at least one further component selected from the group consisting of: arginine; ornithine; cysteine; L-2-oxothiazolidine-4-carboxylate; and omega-3 rich lipids.

6. The enteral product of claim 1 including greater than 15 gms/liter of fiber.

7. The enteral product of claim 1 wherein the product provides at 1500 ml of product the U.S. RDA of all vitamins and mineral except magnesium.

8. The enteral product of claim 7 wherein the product provides at 1500 ml of product approximately 150 to about 250 mg of magnesium.

9. An enteral tube-fed product for providing nutritional needs to a patient comprising:

a caloric content of approximately 0.5 to about 0.8 Kcal /ml;

an osmolality of approximately 100 to about 250 mOsm;

a protein content of greater than 17% of the total calories;

a fat content of greater than 33% of the total calories; and a fiber content of greater than 15 gms/liter.

10. The enteral tube-fed product of claim 9 wherein fiber includes one or more components selected from the group consisting of: insoluble soy polysaccharide; soluble pectin; hydrolyzed plant gum; carob pod; and tannin-enriched extract of carob pod.

11. The enteral tube-fed product of claim 9 wherein the composition includes at least one further component selected from the group consisting of: arginine; ornithine; cysteine; L-2-oxothiazolidine-4-carboxylate; and omega-3 rich lipids.

12. The enteral tube-fed product of claim 9 wherein the protein content is approximately 18 to about 25% of the total calories.

13. The enteral tube-fed product of claim 9 wherein the fat content is approximately 35 to about 50% of the total calories.

14. The enteral tube-fed product of claim 9 wherein the product provides at 1500 ml of product the U.S. RDA of all vitamins and minerals except magnesium.

* * * * *